United States Patent [19]
Farmer

[11] 4,384,576
[45] May 24, 1983

[54] VENTILATOR APPARATUS
[75] Inventor: Robert B. Farmer, Boulder, Colo.
[73] Assignee: Thompson Respiration Products, Inc., Boulder, Colo.
[21] Appl. No.: 234,306
[22] Filed: Feb. 13, 1981
[51] Int. Cl.³ .............................................. A61M 16/00
[52] U.S. Cl. ................................ 128/205.18; 92/13.1; 92/13.7; 74/828; 417/426; 417/429; 417/212; 137/531
[58] Field of Search ....................... 128/204.21, 205.13, 128/205.14, 205.15, 205.18, 205.24, 204.23; 92/13.1, 13.7; 74/828; 417/426, 429, 212; 137/531, 535

[56] References Cited
U.S. PATENT DOCUMENTS

| | | | |
|---|---|---|---|
| 2,159,484 | 5/1939 | Levy | 137/535 |
| 2,640,425 | 6/1953 | Saalfrank | 74/828 |
| 3,818,806 | 6/1974 | Fumagalli | 92/31.7 |
| 3,905,362 | 9/1975 | Eyrick et al. | 128/204.21 |
| 4,076,021 | 2/1978 | Thompson | 128/205.18 |
| 4,243,029 | 1/1981 | Apple | 128/205.18 |

Primary Examiner—Henry J. Recla
Attorney, Agent, or Firm—Klaas & Law

[57] ABSTRACT

A portable positive displacement respirator/ventilator is provided for both a pressure sigh and a volume sigh of predetermined duration and frequency by providing a variable length crank arm connecting a piston through a connecting rod by mounting the connecting rod on a circular toothed gear, pivoting the gear for movement at its center and driven on its outer edge with a separate motor driven pivot gear which when moved relocates the effective length of movement of the point of attachment of the connecting rod thereby changing the volume swept by the piston for the same arc of reciprocal movement of the larger circular toothed gear enabling both a volume change or a volume sigh with the device. A cooperating multiplicity of adjustable pressure regulating valves where at least one can be intermittently closed during the operation of the device regulates ventilation pressure or breathing pressure and sigh pressure.

1 Claim, 16 Drawing Figures

VENTILATOR APPARATUS

BACKGROUND OF THE INVENTION

This invention relates to respirators and ventilator equipment generally and in particular to an improved portable apparatus for assisting normal respiration in patients requiring such devices by the provision of both a pressure sigh and a volume sigh feature in a positive displacement respirator.

Prior portable positive displacement ventilators which have found acceptance have attempted to provide, with varying degrees of success, a so-called pressure sigh function, and some have provided a volume sigh function; but, the flexibility of reliably providing for both functions in a single unit so as to be adaptable to a large proportion of the population of ventilator users is important. Larger institutional devices employing enclosed bellows structures and the like kinds of apparatus with complex structure and controls including for example, supplemental turbine blowers, have been provided; however, these have not been easy to reduce in size effectively so the use of a portable unit has generally meant that certain desirable and often necessary features would not be present in the unit.

Further, some of the smaller positive displacement devices which have incorporated a variable volume capability have utilized either apparatus which have required the motor to be stopped during alteration of the effective radius of a crank arm which connected a connecting rod driving a piston or if designed to be run continuously have employed a variety of mechanisms for changing the effective radius of the crank arm for example, by stepwise mechanical movement of a jack screw during the revolution of the crank by means of impact engagement with mechanical activator tongs. These solutions have not been satisfactory for several reasons including the speed of the change, reliability and suitability for a variety of medical indications.

While it is desirable and therefore an objective of such devices to have continuous, reliable uninterrupted functioning of a positive displacement ventilator it is also a prime objective of such devices to be able to provide adjustment of the volume of air delivered in a predetermined timed relationship while simultaneously providing pressure protection for the patient regardless of the primary mode of function of the device.

There is extensive medical literature concerning the desirability and indeed the need for apparatus to have the capacity for an adjustable volume.

It is therefore one of the primary objectives of this invention to provide a portable ventilator respirator apparatus of the positive displacement type which reliably can provide for a pressure or a volume sigh by the provision of structure enabling the attainment of an adjustable volume or pressure while providing patient protection against excessive pressure. The foregoing is accomplished according to this invention in a rigid cylinder piston pump positive displacement respirator having means for controllably varying the length of the piston stroke from one predetermined first swept volume to another larger second swept volume and then back to the first swept volume in a timed sequential manner while providing means for preselecting a maximum delivery pressure when in either sigh cycle. Large capacity adjustable dump valves are also provided wherein a preselected timed sequential sigh can controllably be provided, wherein volume in excess of the patients requirements can be selected. For example, the ventilation pressure limit can be set to provide the required volume pressure relationship needed by the patient and dump the excess. A sigh pressure limit can also be set to provide an increased volume of air to the patient for a predetermined interval and frequency.

DETAILED DESCRIPTION OF THE DRAWINGS

Figure 1:
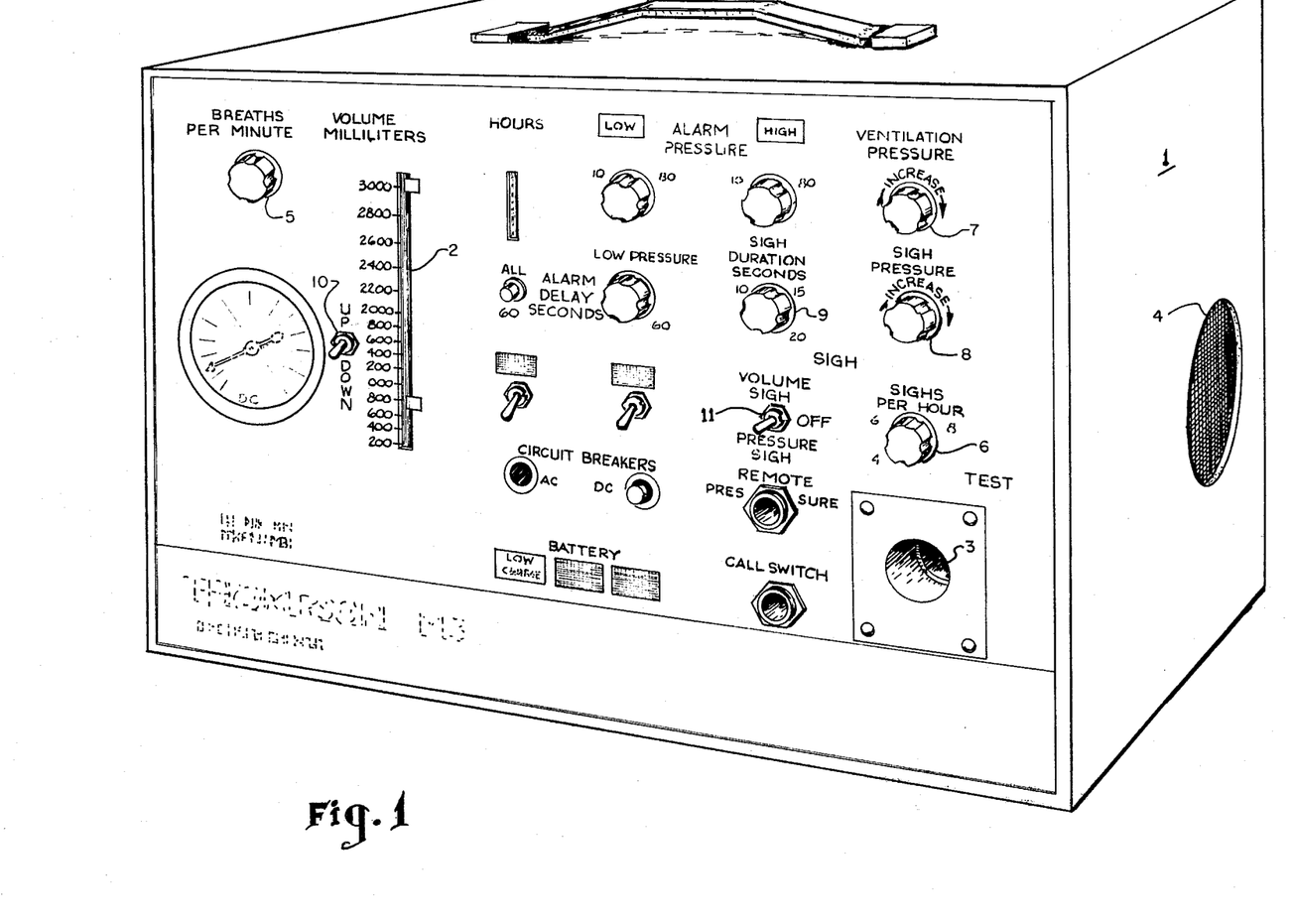
FIG. 1 is a perspective view of the front panel and controls of the respirator of the present invention.

In FIG. 1, the respirator housing (1) is shown and which typically contains a volume indicator (2), an outlet (3) for connection to a patient, an inlet for receiving fresh air, various control knobs; such as a control knob (5) for breathing rate adjustment, a control knob (6) for a sigh per hour adjustment, control knobs for ventilation pressure (7); sigh pressure (8), and sigh duration (9).

In addition, switches are provided for increasing and decreasing volume (10) and for selecting between a volume sigh and a pressure sigh (11). Other controls for various safety features aspects and other functional aspects of the device are also provided.

Figure 2:
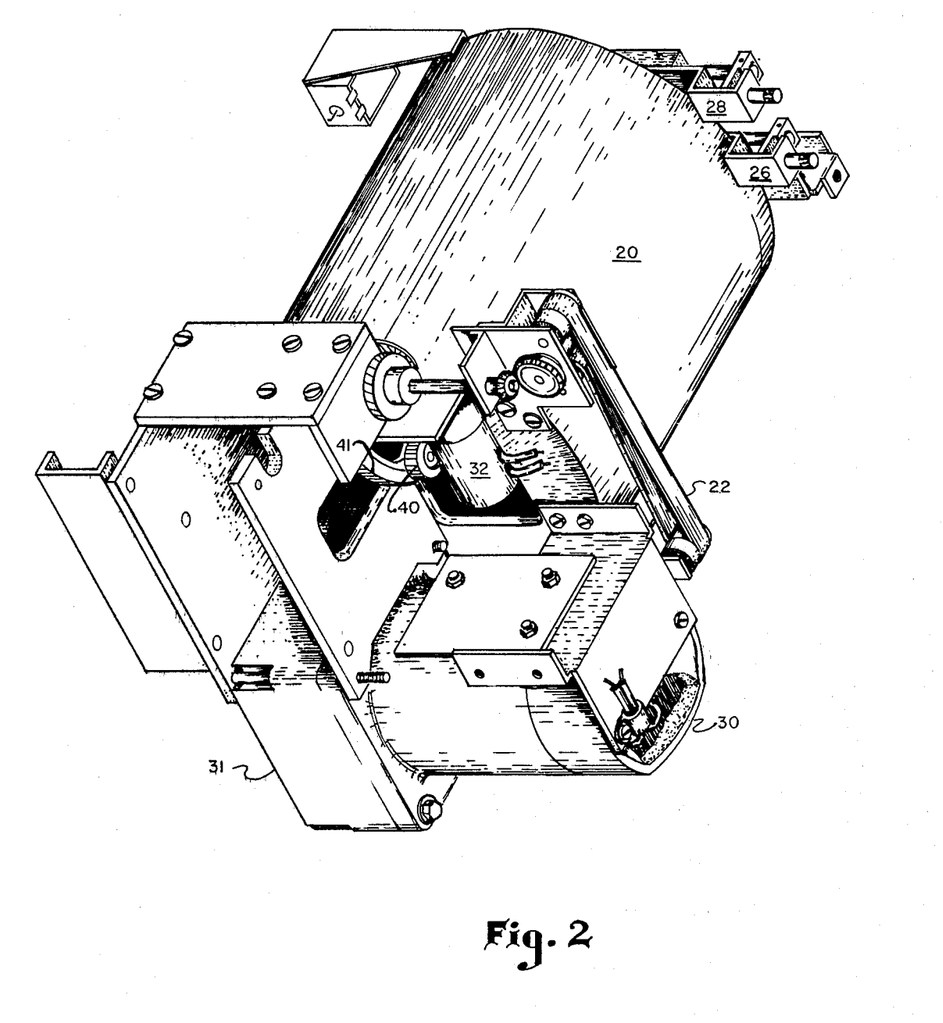
FIG. 2 is a partial perspective view of the inside of the respirator viewed from the above left hand end of FIG. 1.

Referring now to FIG. 2, the orientation of this perspective drawing was selected for better visualization of the mechanical components. The foreground of the drawing being the left hand side of FIG. 1 with the housing as well as the control circuitry removed. The cylinder (20) for housing a piston (80) (shown in FIG. 7) is shown with the ventilation pressure control (28) and the sigh pressure control (26) at the upper right with the volume indicator (22) shown near the rear of cylinder (20) in a position in registry with the volume indicator(2) on the front panel of FIG. 1. The motor (30) and motor gear box (31) are in the position they would occupy in the lower left hand side of FIG. 1. A stroke adjusting motor (32) which is operated in a manner that will be more fully explained hereinafter to increase or decrease the length of the stroke of the piston within cylinder (20), is provided with a direct connection for a visual indication on indicator (22) of the volume setting for the respirator. Piston connecting rod (40) is attached for rotational movement to gear (41).

Figure 3:
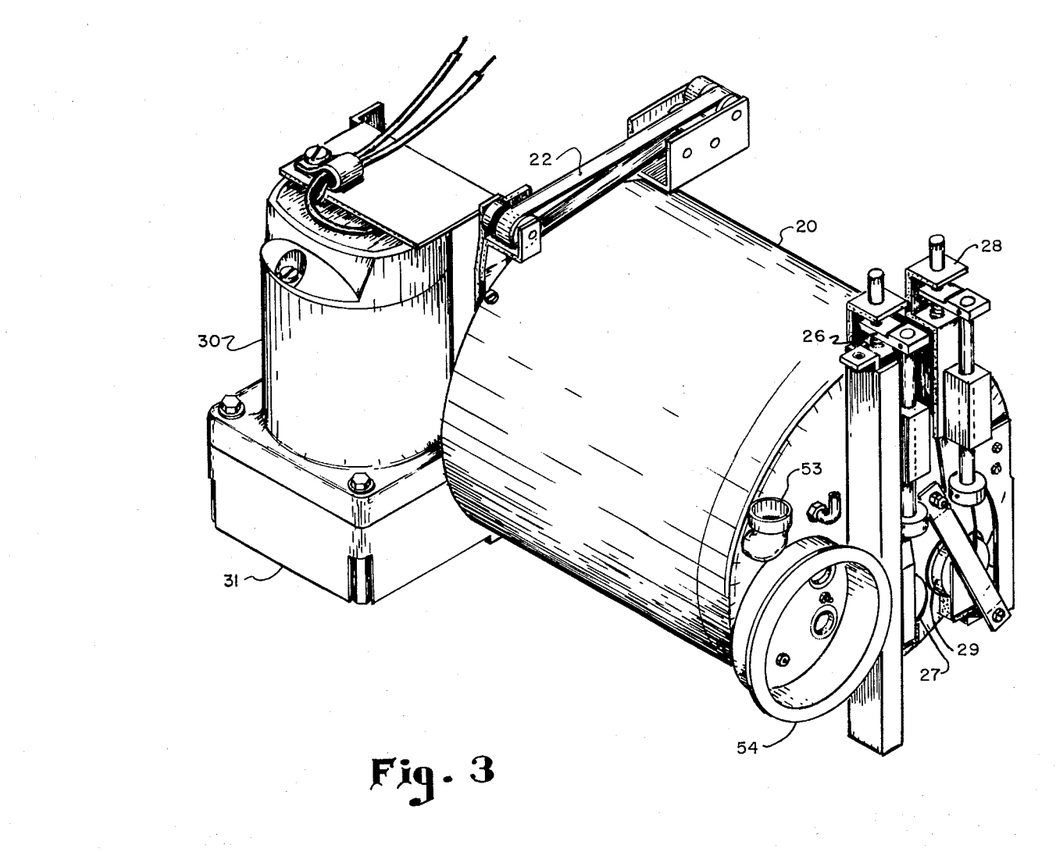
FIG. 3 is a partial perspective of the inside of the respirator viewed from the bottom right hand end of FIG. 1.

Referring to FIG. 3, the orientation of this view is such as to be viewing the components of the inside of the respirator from the bottom right of the housing of FIG. 1 and shows the motor 30 and motor gear box (31) as well as the volume indicator (22) and cylinder (20). The outlet (53) for air from the device is provided to be in registry with the outlet (3) on the housing (1) and the intake (54) with inlet (4). The pressure control (28) is shown with its associated structure for adjusting the pressure on pressure valve (29) and the sigh pressure adjustment (26) with its associated structure for the adjustment of sigh pressure valve (27). The right end view of the respirator of FIG. 1 is shown more clearly in FIG. 4 where the intake (54) is shown with the intake valve seats (55) and (55) attached to the cylinder head. A rubber flapper check valve (not shown) is attached by screw and nut 81 inside of the cylinder head. This with seats (55) and (55) cooperate to act as an intake valve. A flanged cup (56) is provided for intimate contact with the inside of housing (1) in registry with the inlet (4) (FIG.1). The cup (56) is fastened to the end of the cylinder (20) by means of bolts and nuts shown generally as (57). The valves (27) and (29) are spring biased in the closed position on spring (47) and spring (49) which are damped by foam pads (42) and (43) at their extremities. Adjustment of the force of the spring (47) is achieved by turning sigh pressure control knob (8) in a clockwise direction to rotate shaft (44) which has a threaded portion to which is attached a threaded tang (45) attached to a second shaft which is received through a guide block (46) and terminates in an upset or collar which bears on an inclined portion of the spring (47) so that lateral movement of the integral shaft and collar (50) in the direction of valve (27) applies more spring force to the valve thereby permitting higher pressures to be reached within the cylinder (20) before the force of the air pressure overcomes the force on the valve (27) and releases the pressure back to a predetermined amount. Normal ventilation requires a less high pressure setting than that provided by the valve (27) which is set at a predetermined sigh pressure; so additional structure is provided (see FIG. 5) for additional control of the valve (29) since its comparible structure for spring biasing valve (29) into a closed position will generally be set for a lower spring force and therefore a lower pressure maximum. To produce a pressure sigh therefore it is necessary to provide control circuitry (not shown) which is responsive to the control knob (6) in setting sighs per hour and in association with such a timed relationship for the frequency and duration of sighs, electrical actuation of a selenoid (51) pulls bar (52) down onto valve 29 disabling the ventilation pressure setting and thereby permitting the pressure to rise until released at the pressure preset by the adjustment of sigh pressure control (26) acting on spring (47) which exerts a predetermined force against the opening of valve (27). Bar (52) is loosely mounted for a limited predetermined and adjustable movement by the bolt and nut combination (48) so that the end of the bar (52) which is moved by the action of the selenoid (51), essentially overrides the normal release of the pressure through valve (29). The pressure outlet (60) is provided for connection to the pressure gauge and pressure switches shown in FIG. 16.

Figure 6:
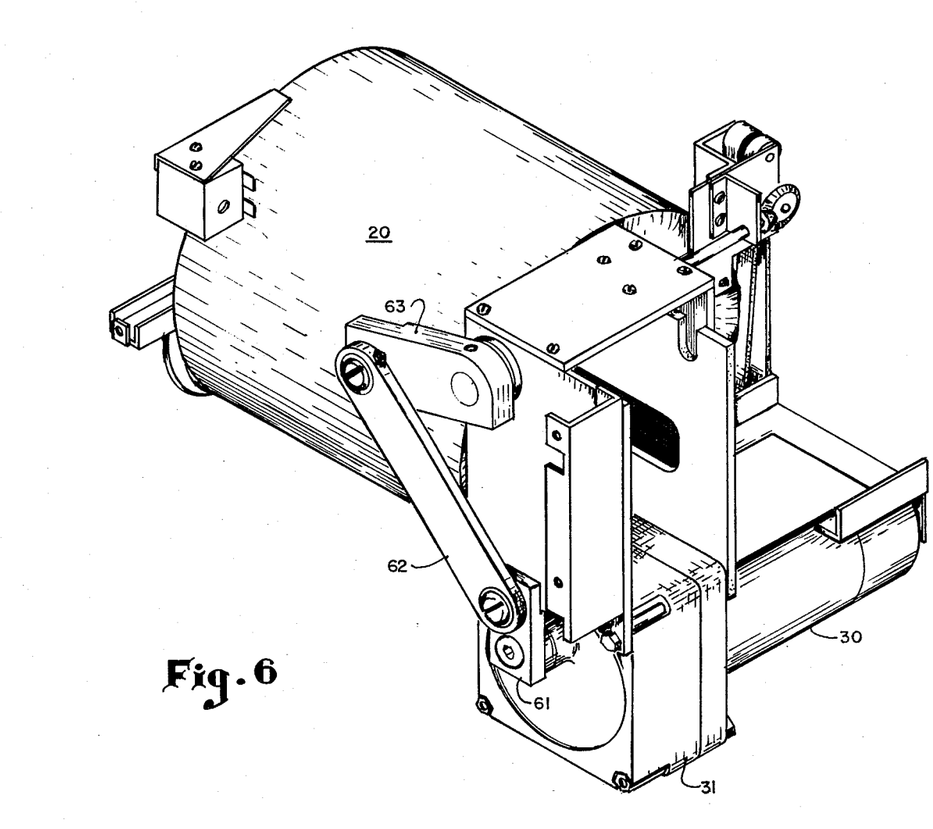
FIG. 6 is a partial perspective view of the inside of the respirator viewed from the left rear of FIG. 1.
Figure 7:
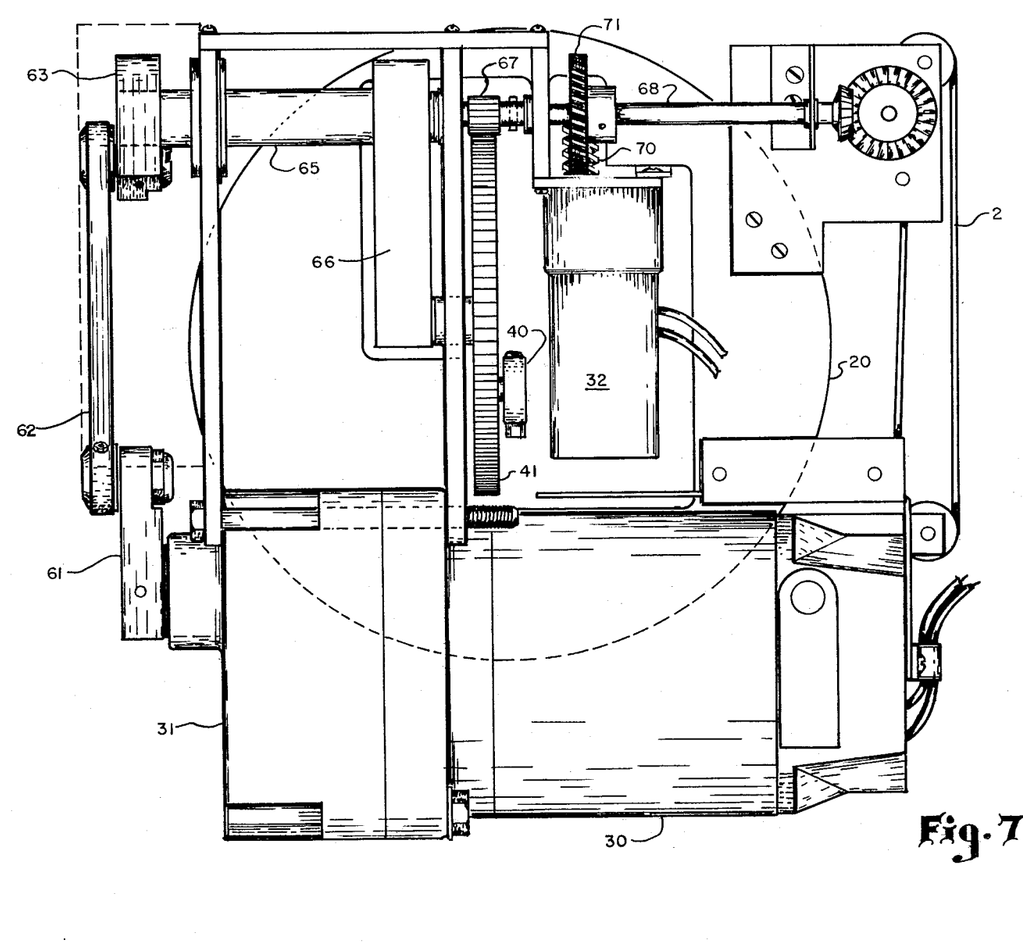
FIG. 7 is a partial left hand end view of the inside of the respirator of FIG. 1.
Figure 9:
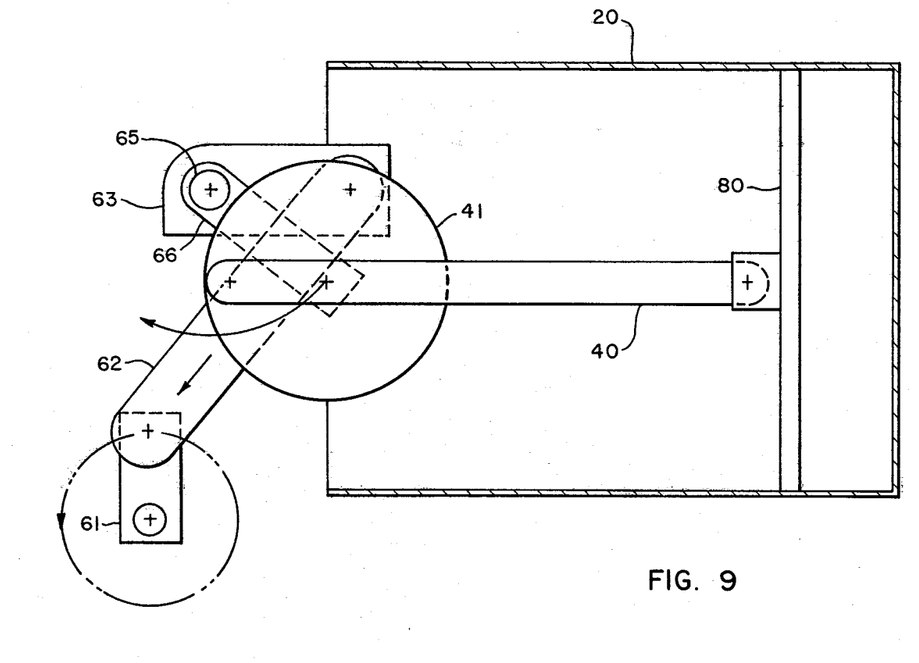
FIG. 9 is a schematic representation of one position of the major mechanical components of the respirator.
Figure 10:
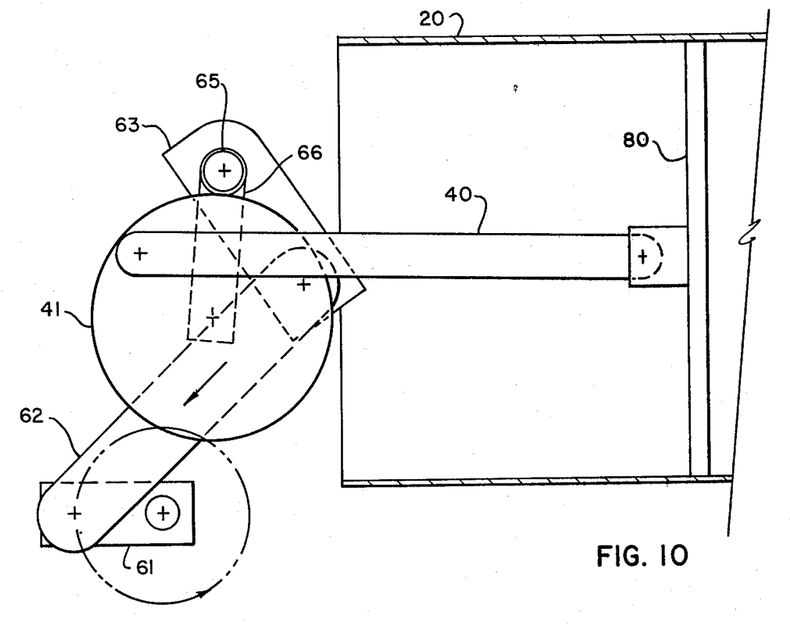
FIG. 10 is a schematic representation of another position of the major mechanical components of the respirator.
Figure 11:
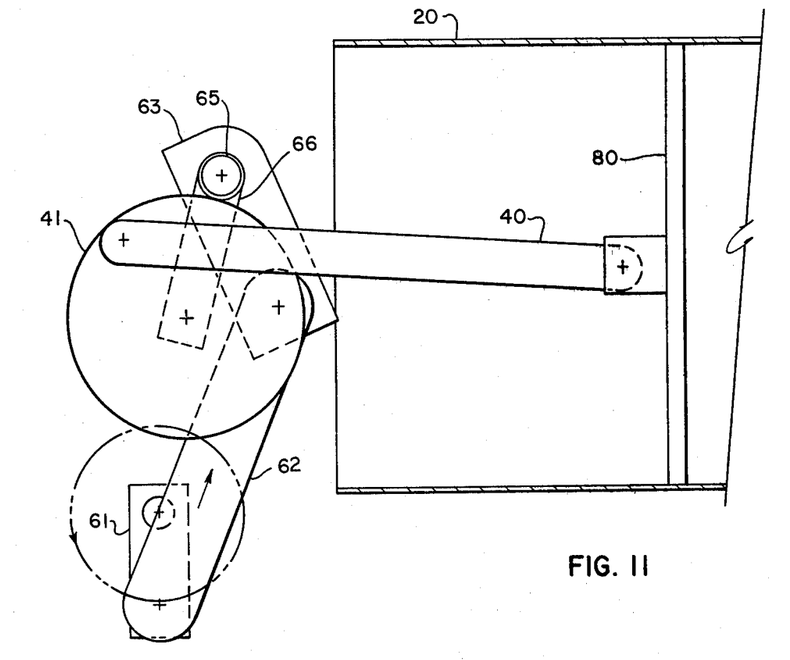
FIG. 11 is a schematic representation of another position of the major mechanical components of the respirator.

Referring now to FIGS. 6 and 7, the variable stroke aspect of the present invention will become clearer. The motor (30) appropriately energized will transmit rotary motion through a suitable reduction gear box where a gear box output shaft (not shown) is attached to a short crank (61) to which is attached a long connecting rod (62) and an intermediate crank (63). This latter crank by the action of the motor (30) imparts limited reciprocal rotational movement to shaft (65). The whole purpose of the connecting rod and crank arrangement is therefore to translate the rotational movement of a motor shaft in motor (30) into a predetermined amount of reciprocal rotational movement in the shaft (65) which in turn moves crank (66) reciprocally through a limited arc. Gear (41) is rotationally mounted on crank (66) and pivots at a tangent to its upper surface about pivot gear (67) which is mounted on shaft (68) whose centerline is in line with shaft (65). The output shaft of stroke adjusting motor (32) is filled with a worn gear (70) which drives gear (71) mounted on shaft (68) which in turn can rotate pivot gear (67) to rotate gear (41). Shaft (68) also drives the volume indicator (2).

Figures 5, 8:
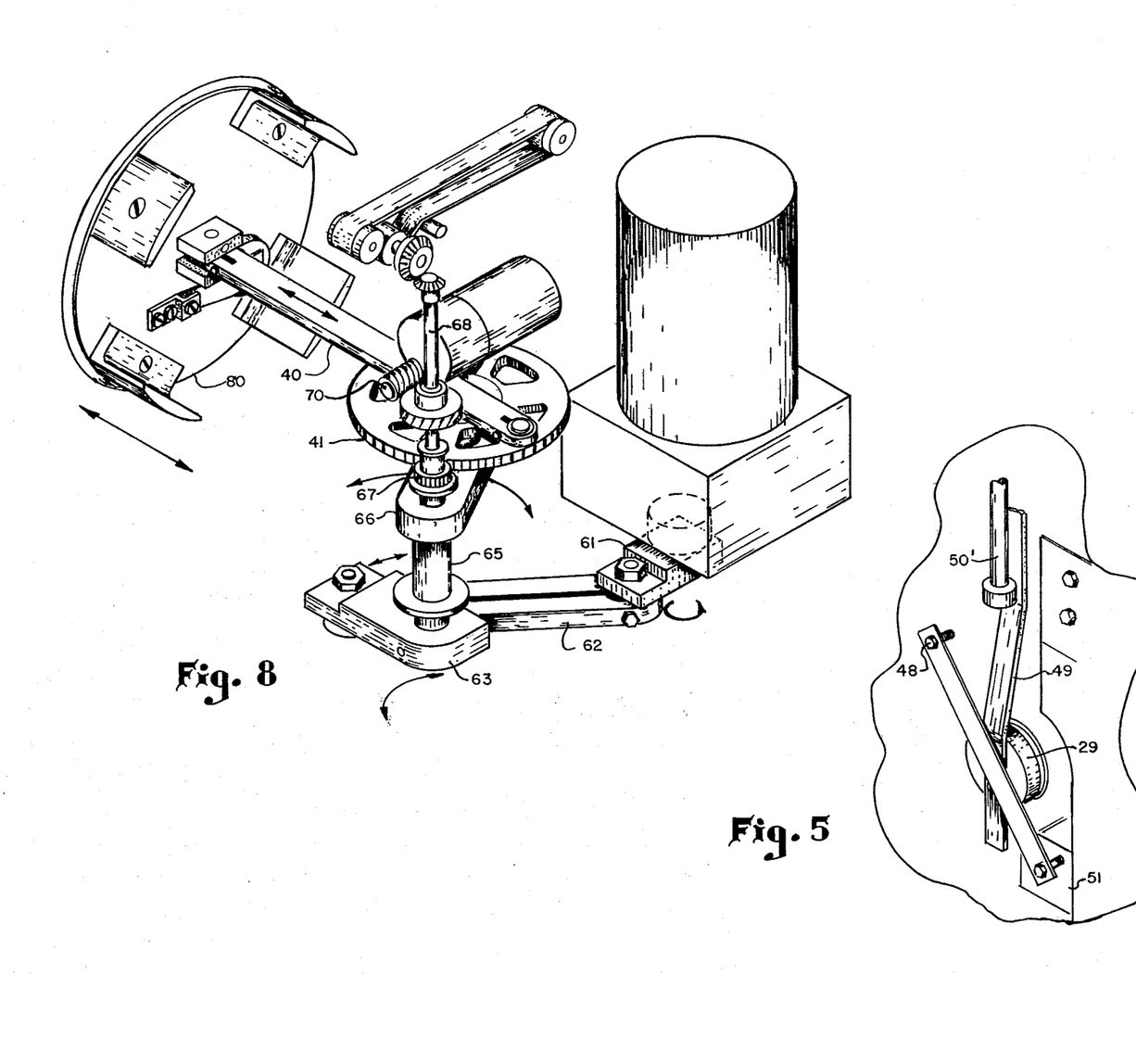
FIG. 5 is a partial perspective view of the adjustable pressure release valve of the respirator shown in FIG. 4.
FIG. 8 is a partial perspective view of the mechanism of the respirator viewed from the left front and above in the position viewable if the respirator of FIG. 1 were laid on its back surface.

As will be seen more clearly in FIG. 8 a rotation of crank (61) moves connecting rod (62) reciprocally to move crank (63) through a limited arc. This rocking motion is imparted to the shaft (65) attached to the crank (63) which in turn moves crank (66) and the attached gear (41) through a limited arc. The connecting rod (40) is attached to the gear (41) as shown in FIG. 7 and in turn to piston (80) which is received for reciprocal movement in cylinder (2) so that the movement of the piston (80) pumps air from inlets (55) and (55') through outlets (53) and (60) according to the description of the invention described herein.

Figure 13:
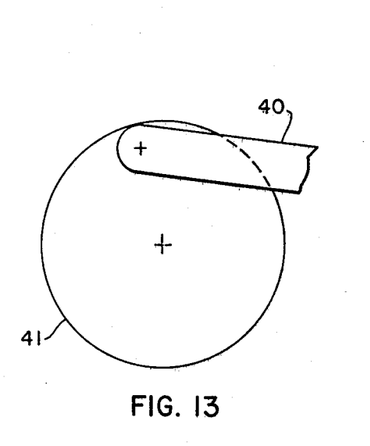
FIGS. 13, 14, and 15, are schematic representations of the wide variety of positions possible for the connecting rod shown in FIGS. 8, 9, 10, 11, and 12.
Figure 14:
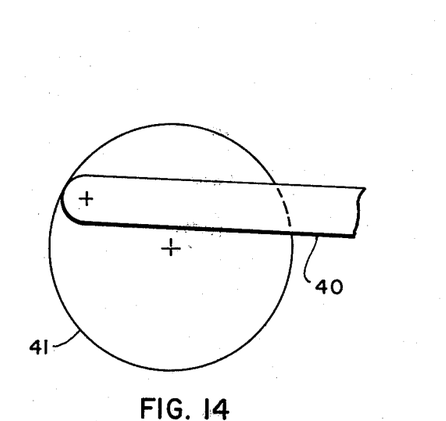
Figure 15:
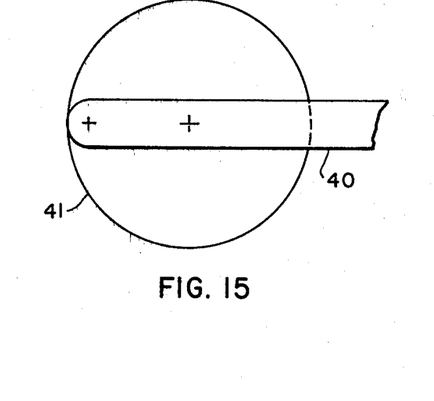

Referring now to FIGS. 9, 10, 11, and 12, the sequence of the movement of the interconnected and interrelated structural elements of FIG. 8 can be seen. With the piston (40) in its starting position, crank (61) rotating counterclockwise, begins to pull the piston (80) back on the intake stroke by the movement of the connecting rod (62), the crank (63), the crank (66), the gear (41) and the connecting rod (40); from the respective positions shown in FIG. 9 to the positions shown in FIG. 10. Further movement of the crank (61) to the position shown in FIG. 11, completes the intake stroke of the piston (40) and begins the exhaust stroke. It is important to note the fixed positions of crank (63) and crank (66) with respect to each other as they both respond to the movement of connecting rod (62) and through their respective fixed connection to shaft (65) provide for the lateral movement of gear (41) and connected connecting rod (40) even though the connection of connecting rod (40) and gear (41) is freely rotatable. Assuming the same sequence of movement of each of the parts shown and described in FIGS. 9, 10, 11, and 12 it will now be readily apparent that the position of the connection between connecting rod (40) and gear (41) in relation to the centerline of shaft 65 will determine the lateral length of the stroke of the piston (80) within the cylinder (2). Within the limits imposed by the radial size of gear (41), the length of the stroke and therefore the volume swept by the piston (80) can be changed. Referring to FIGS. 13, 14, and 15; the movement of the worm gear (70) (FIGS. 6 and 7) will rotate spur gear (67) on shaft (68) thereby rotating the gear (41) into an infinite variety of positions which are representatively shown in FIGS. 13, 14, and 15. In this manner the gear (41) will pivot at the pivot gear (67) thereby providing for an infinitely variable length moment arm which results in variations in the volume swept in cylinder (20) by piston (8). When a reduction in volume is desired it is preferable to incorporate into a ventilator device the ability to locate the excursion of the piston nearer to the closed end of the cylinder head in order to provide for as small a dead air space as possible during operation at small volume settings. The apparatus of the present inventions attains this goal.

Figure 16:
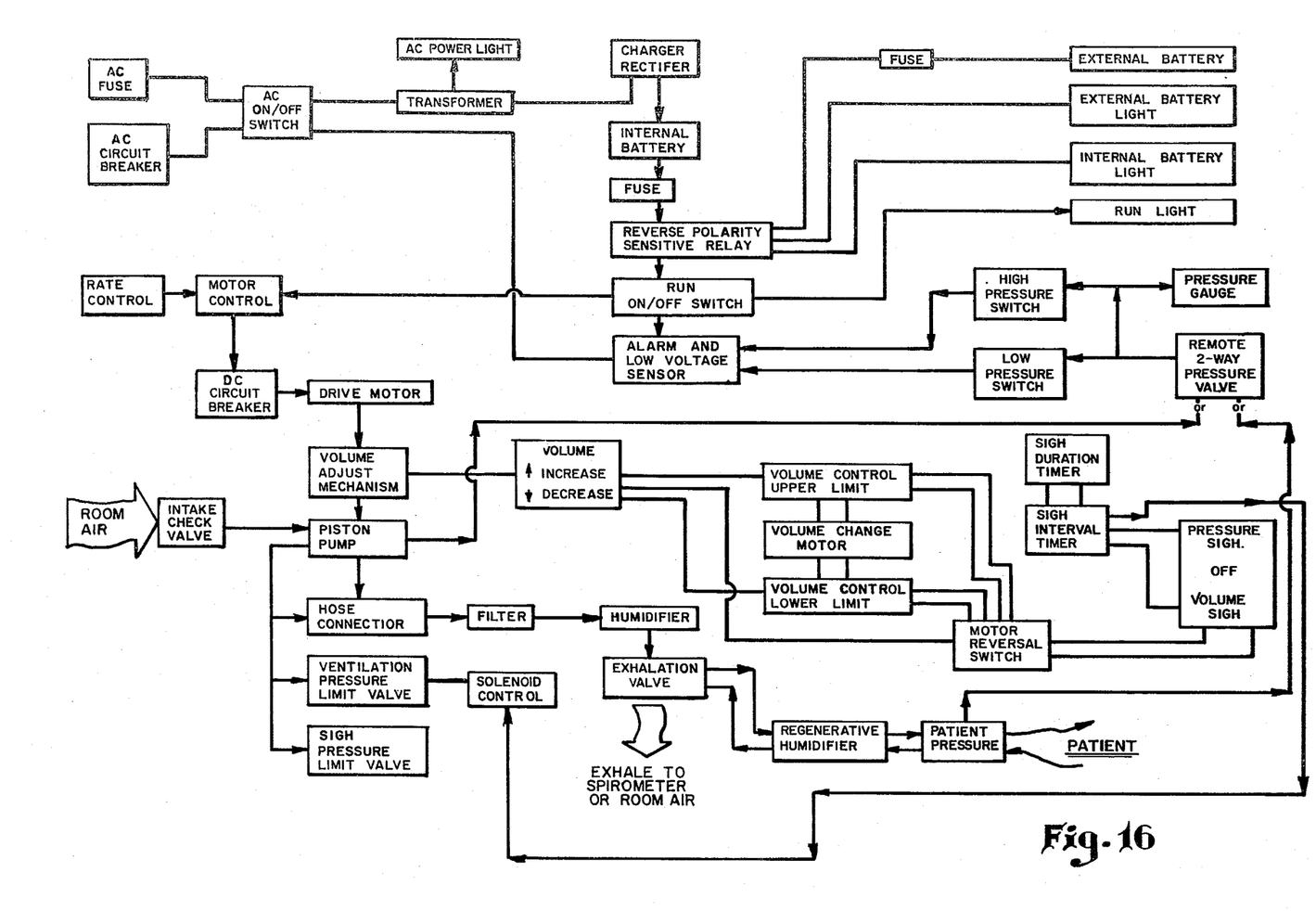
FIG. 16 is a schematic of the control functions of the device.

The overall control functions for the respirator of the present inventions are schematically represented and labeled in FIG. 16. The control of the volume changing motor and its relationship to the normal functions of a respirator which is not so equipped can be clearly appreciated and the selection of specific individual component parts for performing the specified functions and the selection and construction of the connections and circuitry can be straight forwardly accomplished without undue experimentation. Of course many variations are possible including adding multiple functions to a single control or the like depending on the choice of available control components.

Operation

In operation a respirator is normally set for a normal repetitive rate to conform to normal breathing at a specified volume related to the patient's normal respiratory volume. In this mode a sigh can be produced by changing the volume, i.e., by increasing the volume and permitting the pressure to rise from the normal pressure setting to a new higher pressure setting by actuation of the selenoid hold down shown in FIG. 8 in a timed manner responsive to the mechanism and timing for the increase in the stroke of the piston and therefore the increase in volume.

Figure 4:
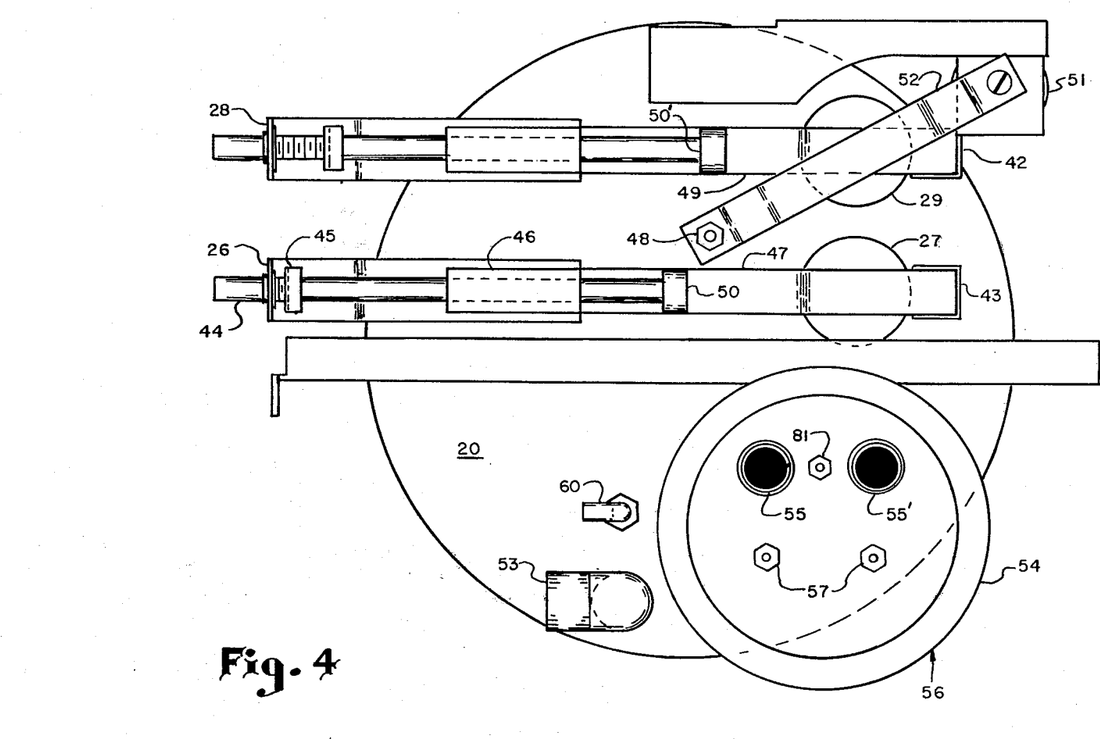
FIG. 4 is a partial right hand end view of the inside of the respirator of FIG. 1.
Figure 12:
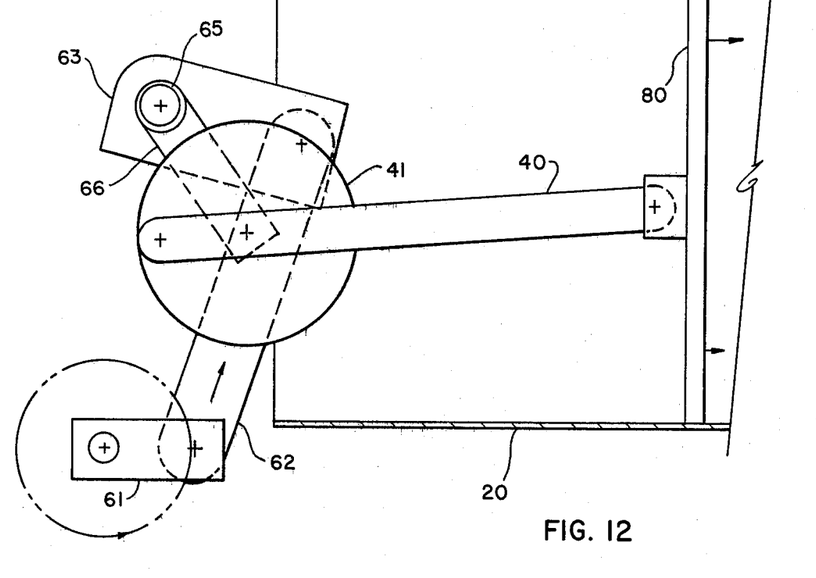
FIG. 12 is a schematic representation of another position of the major mechanical components of the respirator.

Likewise, by reference to the controls in FIG. 12 and the specific structures to which they relate the respirator can be set for a normal breathing rate and volume and for a sigh the volume can be increased beyond the volume desired for the particular patient and present adjustment by the force of the pressure preset as before on the spring (47) in FIG. 4 to the desired protection level thereby dumping the excess to the outside of the system. Again the change in the volume accomplished by the change in the stroke of the piston (80) in response to an adjustable timer (see FIGS. 1 and 10), i.e., three times per hour; or a number of normal breaths and then either a timed sigh or a number of sighs and each period of sigh may have an adjustable duration and must coincide with the actuation of the selenoid and the hold down of the normal pressure valve (29) so that the new higher pressure setting on valve (27) will control the pressure above which exhaust of the excess air will occur.

A given patient may have for example a normal respiration rate of one breath every six seconds and normally requires a sigh twice every twenty five minutes. The respirator according to this invention could then be adjusted to provide two deep breaths or sighs every twenty five minutes which would mean that the pump stroke would have to be varied for twelve full seconds every twenty five minutes to accommodate that particular patient. Obviously, the same setting for a patient who breathed twice as quickly would thus provide four deep breaths or sighs every twenty five minutes. The particular equipment described herein is provided with a wide range of controllable adjustment which will permit adjustment to provide for shorter or longer intervals between sighs and for longer or shorter sigh durations which will of course provide a number of sighs which are dependant upon the respiration rate of the particular patient and the predetermined interval between sighs and duration of the individual sigh or deep breath.

Other modes of possible operation are of course possible with various combinations of volume adjustment utilizing the timed variation in the stroke of the piston in combination with the selenoid operated adjustable breathing pressure valve (FIG. 8) and the adjustable sigh pressure valve used for control and patient protection in either the volume or pressure sigh mode of operation. Likewise the breaths per minute, sigh duration and frequency can be controllably adjusted for any of the previously described modes so as to provide for broad flexibility in use. For example, the respirator of the present invention can be employed with trach patients where there is an air leak around the trach tube. In such a case the breathing volume setting might have to be substantially greater than the normal breathing volume to accommodate for the leak. The patient by voluntarily closing his glottus may stop the leak and the higher volume of air entering the lungs can be pressure regulated by the setting of the sigh pressure valve to dump or exhaust the air above that needed to reach a preset sigh pressure or the patient can accept all the air and set the pressure relief valve for a higher pressure and thereby use the volume limiting feature of the breathing pressure valve.

It can be seen from the foregoing that the wide range of possible applications for the device of the present invention could possibly employ other structure and controls than those disclosed for achieving the same functional result. It is therefore contemplated by this invention that equvalent structure and controls in substitution for those disclosed to utilize some or all of the features of the present invention can accomplish some or all of the objectives of the present invention and the scope of the invention is therefore only limited by the appended claims utilizing such equivalent structures and controls.

What is claimed is:
1. A portable positive displacement respirator comprising:
   a housing,
   a rigid cylinder inside said housing having a normally open end and a normally closed end, said closed end containing means for exhausting air to a patient,
   a piston received in said rigid cylinder adapted for reciprocal movement,
   a piston connecting rod having a first end attached to said piston,
   motive means attached to said piston connecting rod for imparting reciprocal movement to said piston in said cylinder,
   said motive means including means for converting rotary motion into reciprocating motion and means for adjustably varying the length of the reciprocating movement of said piston in said cylinder, said adjusting means being attached to said reciprocating means and being adjustable to establish a predetermined length of stroke of said piston from the exterior of said housing whether or not piston is moved, said adjusting means comprising a shaft rotatably mounted in said housing; said motive means including means for rotating said shaft through limited reciprocal arc movement, a crank mounted at one end to said shaft and responsive to the movement of said shaft, a circular gear mounted for rotational movement near the other end of said crank arm, a pivot gear mounted on said shaft but separately rotatable thereabout, said pivot gear engaging the outer periphery of said circular gear, said piston connecting rod having a second end connected to said circular gear at a position other then its center so that reciprocal arc movement of said shaft is imparted to said connecting rod and wherein said adjustment means includes means for selectively rotating said pivot gear to change and maintain the effective location of the connection of said connecting rod with respect to the location of the center of said circular gear, thereby changing the effective length of the reciprocal movement of said connecting rod without a corresponding change in the size of the arc movement of said shaft.

* * * * *